US00PP12336P2

(12) United States Plant Patent
Heims

(10) Patent No.: US PP12,336 P2
(45) Date of Patent: Jan. 8, 2002

(54) PULMONARIA PLANT NAMED 'MAY BOUQUET'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/628,784

(22) Filed: Jul. 31, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Klarquist Sparkman, LLP

(57) ABSTRACT

A new and distinct hybrid of Pulmonaria plant characterized by silver-spotted foliage and large red-purple flowers to nearly 2 cm wide.

1 Drawing Sheet

The present invention relates to a new and distinct hybrid of Pulmonaria, of the family Boraginaceae, which originated as an open-pollinated cross between Pulmonaria 'Berries and Cream' U.S. Plant Pat. No. 10,597 (seed parent) and an unknown pollen parent. This is known to be an outcross because Pulmonaria does not normally self-pollinate. Due to the fact that the instant plant and parent plants are of hybrid origin, no species designations are given.

This new Pulmonaria is a result of an open-pollinated cross of the aforementioned plants at Terra Nova Nurseries, Inc., in Canby, Oreg. The seed parent plant was retained to observe habit and to compare with the instant plant. The new variety has been reproduced only by asexual propagation (division and tissue culture). Each of the progeny exhibits identical characteristics to the original plant.

This plant is characterized by the following:

1. Large flower size nearly 2 cm from petal tip to petal tip.
2. Silver spotted foliage.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows Pulmonaria 'May Bouquet' in Canby, Oreg.

DETAILED PLANT DESCRIPTION

The following is a detailed description of the new Pulmonaria hybrid based on observations of a one-and-a-half year old specimen grown in a three-gallon pot in Canby, Oreg. The color descriptions are all based on The Royal Horticultural Society Colour Chart.

Plant:

*Type.*—Herbaceous perennial. Retains its foliage in USDA zones 6 and above. Foliage dies down to the ground in USDA zones 4–5.

*Height.*—24 cm (1.5 year old plant grown in a 3-gal pot in Canby, Oreg.).

*Width.*—68 cm (1.5 year old plant grown in a 3-gal pot in Canby, Oreg.).

Leaf:

*Type.*—Simple.
*Shape.*—Lanceolate.
*Length.*—To 22 cm.
*Width.*—To 11.5 cm.
*Petiole length.*—To 16.5 cm.
*Margins.*—Entire. Ciliate. Sporadic undulation.
*Apex.*—Narrowly acute.
*Base.*—Attenuate.
*Leaf texture.*—Setose.
*Petiole texture.*—Setulose.
*Leaf arrangement.*—Rosette.
*Venation.*—Reticulate.

Flower bud:

*Size.*—1.4 cm. long and 0.5 cm. wide.
*Shape.*—Ovoid.

Flower:

*Type.*—Perfect. Complete.
*Shape.*—Funnelform with limbs flared out at right angles to the tube.
*Size.*—To 1.8 cm. wide and deep.
*Corolla.*—5 fused petals with rounded lobes.
*Calyx.*—5 fused sepals, campanulate, parted ⅓ to base, hispid and with glandular hairs, 1.5 cm. deep and 0.6 cm. wide.
*Pistil.*—Exerted or pin type.
*Ovary position.*—Partly inferior.
*Carpel number.*—4.
*Stamen number.*—5, in the tube.
*Inflorescence type.*—Forked cymes.
*Flower number per inflorescence.*—20–30 with 3–5 open at a give time.
*Peduncle width.*—4 mm tapering to 1.5 mm.
*Peduncle texture.*—Setose.
*Blooming height.*—To 18 cm.
*Bloom period.*—Late February to late April in Canby, Oreg.
*Fragrance.*—None.

Seed:

*Type.*—4 smooth nutlets, black and shiny, typical of the genus.
*Fertility.*—Fertile.

Habit: Clumping.

Disease: None observed on plant grown under commercial conditions in Canby, Oreg.
Hardiness: USDA zones 4–9.

Color Characteristics

Foliage:
*Upper surface.*—RHS 139A Green Group.
*Upper surface, spots.*—RHS 188B Greyed-Green Group.
*Lower surface.*—RHS 191A Greyed-Green Group.
Flower:
*Bud.*—RHS 58A Red-Purple Group.
*Corolla.*—RHS 71B Red-Purple Group at the anthesis and turning to RHS 96B-C Violet-Blue Group as it senesces.
*Pollen.*—RHS 155B White Group.
*Calyx.*—RHS 147B Yellow-Green Group.
Peduncle: RHS 146B Yellow-Green Group.
Seed: RHS 202A Black Group.

DESCRIPTION OF PARENT PLANTS

The instant plant resulted from an open-pollinated cross between Pulmonaria 'Berries and Cream' U.S. Plant Pat. No. 10,597 and an unknown pollen parent. Pulmonaria 'Berries and Cream', as described in U.S. Plant Pat. No. 10,597, has markedly ruffled leaves, silver with a thin green margin, and distinctive raspberry-pink flowers in spring. The instant plant differs in having larger flowers and spotted leaf markings.

Compared to Pulmonaria 'Dark Vader' (Plant patent application Ser. No. 09/628,783), the instant plant has a lower, wider habit, more silvering on the leaves, and larger flowers.

Compared to Pulmonaria 'High Contrast' (Plant patent application Ser. No. 09/628,782), the instant plant has larger flowers and less silvering on its leaves.

I claim:

1. A new and distinct hybrid of Pulmonaria plant substantially as shown and described, characterized by a unique combination of silver-spotted foliage and large red-purple flowers to nearly 2 cm wide.

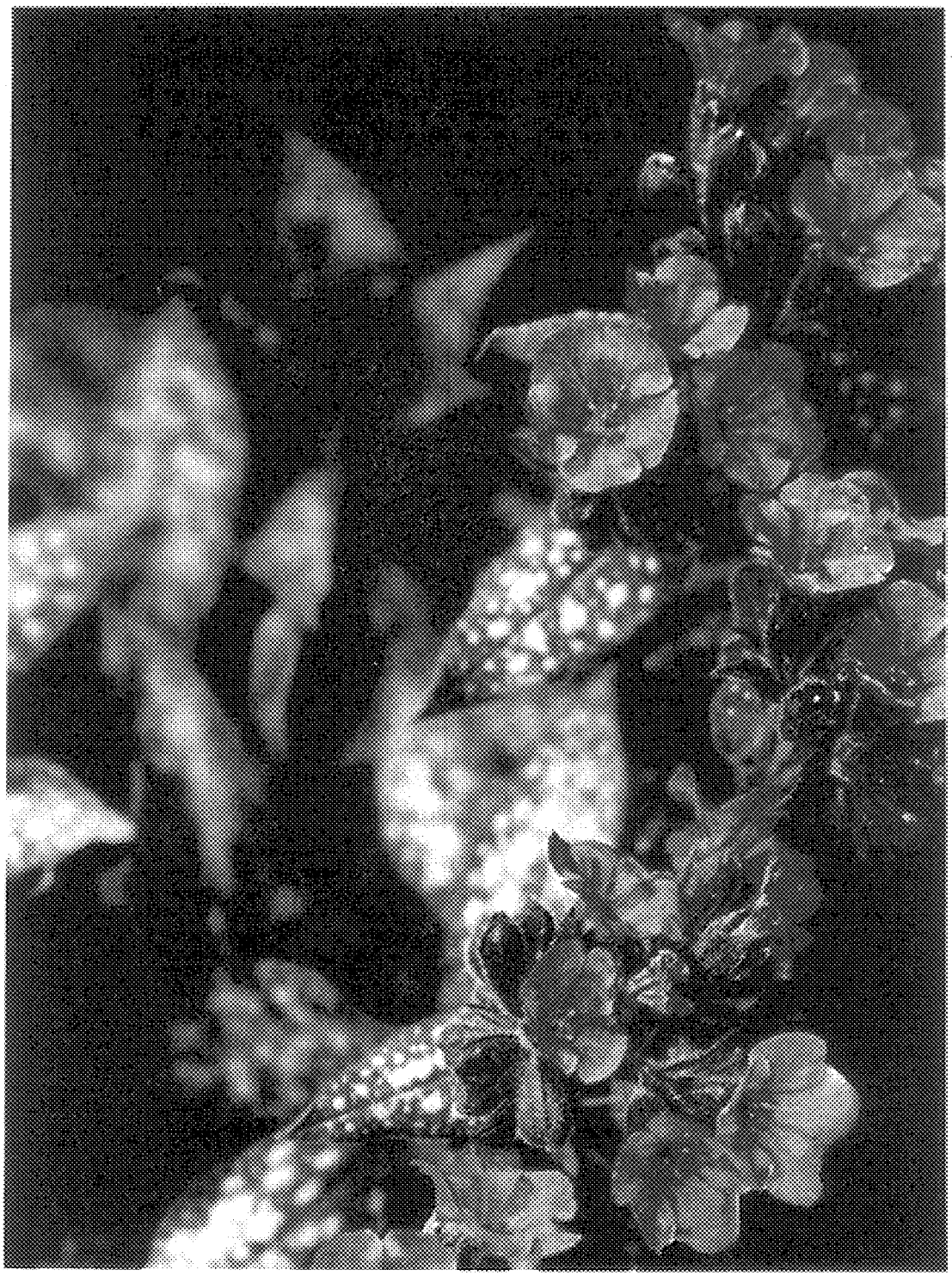

* * * * *